Figure 1:
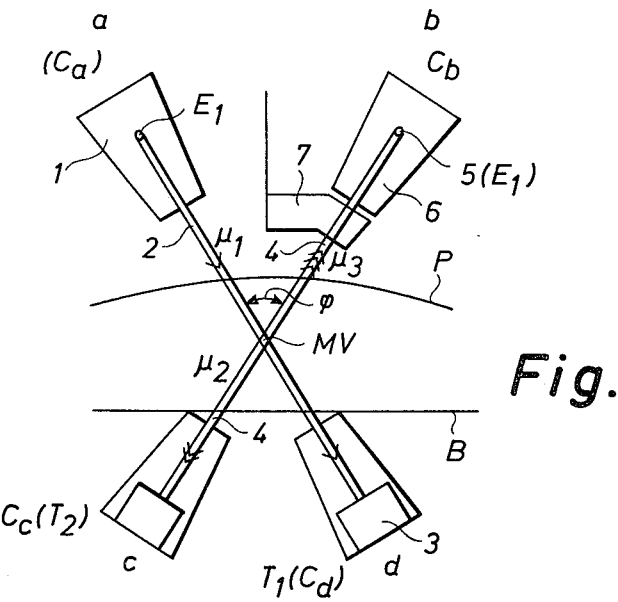

United States Patent

Leunbach

[11] 3,961,186
[45] June 1, 1976

[54] METHOD AND APPARATUS FOR THE DETERMINATION OF ELECTRON DENSITY IN A PART VOLUME OF A BODY

[76] Inventor: Ib Leunbach, Birkholmvej 29, 2720 Vanlose, Denmark

[22] Filed: Sept. 26, 1974

[21] Appl. No.: 509,514

[30] Foreign Application Priority Data
Oct. 9, 1973 Denmark .......................... 5473/73

[52] U.S. Cl. ............................ 250/272; 250/363 S; 250/445 T
[51] Int. Cl.² ........................................ G01N 23/20
[58] Field of Search .......... 250/272, 273, 312, 361, 250/362, 363, 366, 369, 445 T, 313, 358, 306, 307

[56] References Cited
UNITED STATES PATENTS

| | | | |
|---|---|---|---|
| 3,509,341 | 4/1970 | Hindel et al. ....................... | 250/366 |
| 3,809,904 | 5/1974 | Clarke et al. ................... | 250/312 X |

*Primary Examiner*—Davis L. Willis
*Attorney, Agent, or Firm*—Ladas, Parry, Von Gehr, Goldsmith & Deschamps

[57] ABSTRACT

A method of and an apparatus for the determination of the electron density of small volumes of a body. Two narrow beams of ionizing radiation of substantially equal intensity are subsequently directed through the small volume in two different directions. The intensity of the transmitted radiation as well as the scattered radiation along said two directions is measured extra-corporally, which measurements are employed in computing the electron density of the small volume. The employed radiation is of such high energy that the Compton effect will be the wholly dominant absorption phenomenon in the volume as well as in the radiation paths in the two mentioned directions, and that the change in the absorption cross-section from primary to secondary radiation caused by the Compton shift will be substantial.

9 Claims, 8 Drawing Figures

METHOD AND APPARATUS FOR THE DETERMINATION OF ELECTRON DENSITY IN A PART VOLUME OF A BODY

The invention concerns a method for the determination of the electron density, absorption coefficient, or transmission coefficient in desired small portions (part volumes) of a body by means of radiation transmission through the same by a beam of ionizing radiation, by which method the desired part volume, the measuring volume, is penetrated in a first direction by a radiation beam of definite intensity, and where the intensity of the transmitted radiation in the first direction, the primary radiation, is measured extracorporally as well as the intensity of the scattered radiation, the secondary radiation, in a second direction, which forms a certain angle to the first direction, whereupon the measuring volume is penetrated in the said other direction by possibly the same radiation intensity as before, and where the intensity of said other transmitted primary radiation in the other direction is measured as well as the intensity of the secondary radiation in the said first direction, whereby the values of the measured intensities are employed for the calculation of the electron density in the measuring volume.

It is well known that a three-dimensional body when x-rayed is represented by a two-dimensional picture, and that the details positioned between the front and back aspects of the object are reproduced in such a way that they overlap and thereby make the interpretation of the x-ray picture difficult. If the object could be divided by a number of parallel plane cuts with small mutual distance, and the slices thus formed could be examined separately by means of x-rays, it would be possible to observe small differences in the electron density between different tissue structures, which could then reveal possible existing anomalies and thereby facilitate the task of diagnosis. As such physical division into slices is not, however, possible in actual practise more indirect methods must be applied.

It is known in the art to measure the intensity of the secondary radiation which is scattered from an observed part volume of a body which is penetrated by a high energy x-ray or gamma-radiation (Compton effect) and so to obtain a numerical value for the electron density of the part volume. It is known, for instance, from a paper entitled "The Examination of Internal Tissues, using Gammaray Scatter with a Possible Extension to Megavoltage Radiography" in the journal Physics in Medicine and Biology, Volume 4, 1959, p. 159–166 by P. G. Lale to cause a small beam of x-ray to penetrate a body and on its way to penetrate a part volume inside the larger body and to direct the scattered radiation emitted from said part volume through a collimator the slit of which is focused on said part volume. The intensity of the thus scattered radiation is then measured by means of a scintillation detector. The intensity of the scattered radiation reaching the detector crystal depends on

1. the intensity of the primary beam in the measuring volume,
2. the electron density in the tissue within the measuring volume,
3. the absorption degree of the scattered radiation.

It can be shown that provided that the first and the last of said three variables can be kept constant or be compensated for the measuring value in the detector, also termed the count figure, is proportional to the electron density in the tissue in the measuring volume in question.

The disadvantage of said known method, however, is the impossibility of fully compensating for inhomogeneities in the partial areas surrounding the measuring volume, which for the thus known method sets a degree of measurement uncertainty that is unacceptable if the determination of electron density in a part volume within an animal or human body is to provide the basis for reasonably certain diagnosis.

It is further known from the Danish Pat. Application No. 5867/72 and U.S. Pat. No. 3,809,904 that the electron density of a part volume can be determined with a correction at any rate theoretically complete for such inhomogeneities as might surround the measuring volume by means of the method described above. For the method described in the above-mentioned patent application it is a precondition, however, that the Compton shift is negligible, which is achieved by the employment of a low energy radiation of less than 100 KeV.

Employment of radiation as soft as this carries a number of disadvantages, partly radiation-physical and partly economic in kind, of which the most important ones will be stated below.

The employment of low energy radiation will have the effect that multiple Compton processes outside the measuring volume will contribute to the resulting measurement in such a way that the signal-to-noise ratio will be relatively small. This can, as a rule, be counteracted by equipping the detectors with impulse amplitude analyzers, but precisely because the Compton shift is negligible this will be no remedy in the situation described. Inhomogeneities near the measuring volume will therefore give rise to so much noise via multiple scattering processes that the precision will be insufficient for medical diagnosis.

It is a further problem that photo-electric effects in the measuring volume cannot be excluded when low energy radiation is employed. The measured paramether therefore is not well defined, which makes diagnosis even more infeasible.

Finally, it is difficult to point to a monochromatic isotope of suitable low energy the half-life of which is not inconveniently brief. Also, the lower penetration power through the patient and the radiation source itself will mean that the activity level of the quantum emitter must be considerably increased. These latter factors make it economically impossible to employ known isotopes as radiation sources. There remains the use of x-ray tubes, but as they are not monochromatic the requisite employment of impulse amplitude analyzers with very small window widths necessarily leads to a wholly unacceptable increase of the patient-dosage as well as an increased cost of the electronic components so that this is not a solution to be recommended either.

The purpose of the present invention is to provide a method which will overcome all the disadvantages described here. The present invention provides for a method for the determination of the electron density, absorption or transmission coefficient of desired small volumes (partial volumes), called the measuring volume, of a body comprising the steps of directing a first beam of ionizing radiation through said measuring volume to penetrate said volume in a first direction by said first beam having a definite intensity $I_0$; measuring extra-corporally the intensity of the radiation transmitted through said volume in said first direction, the primary radiation, as well as the intensity of a scattered radiation in a second direction, the secondary radiation, said second direction forming a certain angle $\phi$ to said first direction; directing a second beam of ionizing radiation substantially of said definite intensity $I_0$ through said volume in said second direction; measuring extra-corporally the intensity of said second beam transmitted through said volume in said second direction, the primary radiation, as well as the scattered radiation of said second beam in said first direction, the secondary radiation, thus employing such high energy radiation that the Compton effect will be the wholly dominant absorption phenomenon in said volume as well as in the radiation paths in said first and second directions, and that the change in the absorption cross-section from primary to secondary radiation caused by the Compton shift will be substantial; and employing the values of said measured intensities to calculate the electron density of said measuring volume.

By the employment of high energy radiation it is thus precluded that the photo-electric processes become appreciably important and with this precondition it can be shown that the formula for the electron density n in any part volume can be given as $$n = K \cdot [C_a \cdot C_b \cdot C_c \cdot C_d]^{1/4} \left[ \frac{C_c \cdot C_d}{C_a \cdot C_b} \right]^{\frac{2\mu_1 + \mu_3 - \mu_2}{4(\mu_2 + \mu_3)}} \left[ \frac{A_o^2}{T_1 \cdot T_2} \right]^{\frac{\mu_2(\mu_1 + \mu_3)}{2\mu_1(\mu_2 + \mu_3)}} A_o^{-1} \quad (1)$$

in which $K =$ a calibration constant
$\mu_1 =$ the total linear attenuation coefficient for primary radiation
$\mu_2 =$ the total linear attenuation coefficient for Compton radiation "forwards"
$\mu_3 =$ the total linear attenuation coefficient for Compton radiation "backwards"
$A_o =$ an arbitrary expression for the power of the radiation source, and
$C_i$, $T_i$ are measure figures or count figures.

The attenuation coefficients $\mu_1$, $\mu_2$, and $\mu_3$ can be found in a table.

It can further be proved that the exponent for the measure figures $C_a$ and $C_b$ for a suitable choice of radionucleid and diffraction angle $\phi$ are so small that their measurement can be omitted since even a very rough estimate of these quantities will influence the determination of n only to a very small degree.

The formula can then be approximated as follows:

$$\left\{ n = K \left[ \frac{C_c \cdot C_d}{(T_1 T_2)^{\mu_2/\mu_1}} \right]^{1/2} \right\} \quad (2)$$

It will be seen that the formula used in connection with the known low energy method expresses only a special case of equation (2), namely when $\mu_1 = \mu_2$, which is, of course, practically the definition of low energy radiation since $\mu_1 = \mu_2$ expresses the circumstance that the attenuation coefficient of primary radiation equals the attenuation coefficient of the forward Compton radiation.

By the employment of high energy radiation is obtained also a substantial Compton shift between the primary and the secondary radiation so that the noise from inhomogeneities near the measuring volume can be eliminated by a filtering. Hereby is obtained that the required measuring precision is obtainable.

Finally, a suitable monochromatic isotope with a relatively long half-life (30 years) can be pointed to as a high energy radiation source. This fact affords the possibility of producing an apparatus on a basis which is both medically and economically sound.

The present invention further provides for an apparatus for carrying out the method according to any one of the preceding claims, the apparatus comprising a first and a second radiation source for the successive emission of a first and a second beam of ionizing radiation directed towards a partial volume to be examined, the measuring volume, which first and second beams together form a certain angle $\phi$, means for alternately screening said first and said second radiation source, a first detector placed diametrically opposite the first radiation source with respect to the measuring volume for measuring the intensity of the transmitted primary radiation from said first radiation source, a second detector placed in the radiation path of said second radiation source for measuring the intensity of said secondary radiation originating from said first primary radiation transmission through said measuring volume, as well as a third detector placed in the radiation path of said first radiation beam for measuring the intensity of said secondary radiation originating from said second primary radiation transmission through the measuring volume, and a fourth detector for measuring the intensity of the transmitted primary radiation from the second radiation source, means for registering the measured values, said apparatus further comprising means for producing a radiation of such high energy that the Compton effect will be the wholly dominant absorption phenomenon in the measuring volume as well as in the primary and secondary radiation paths, and that the change in the absorption cross-section from primary to secondary radiation caused by the Compton shift will be substantial.

Furthermore, the apparatus is preferably supplied with means for the processing of measured values for the calculation of electron density in the measuring volume examined as well as with means for outputting the result and possibly scanning means.

Figure 2:
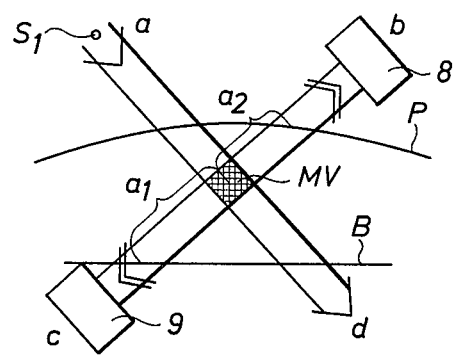
Figure 3:
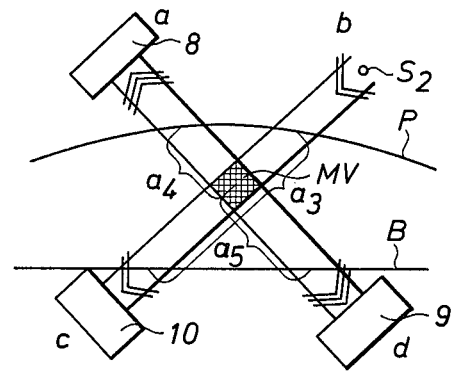
Figure 4:
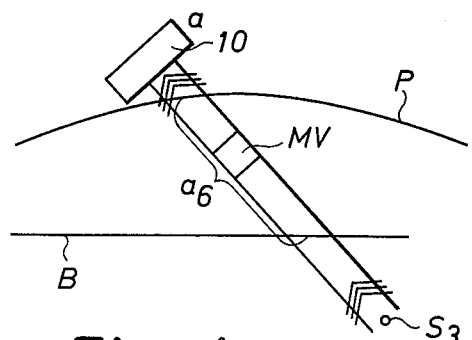
Figure 5:
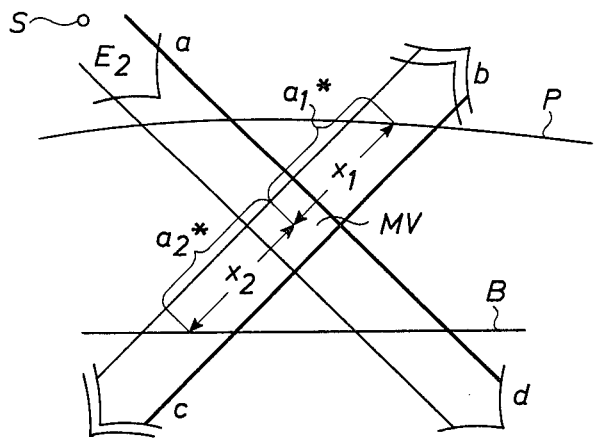
Figure 6:
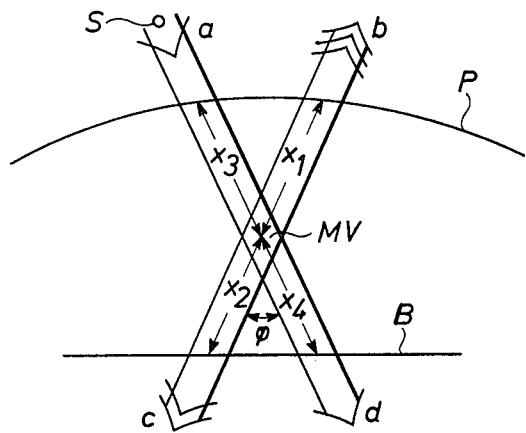
Figure 7:
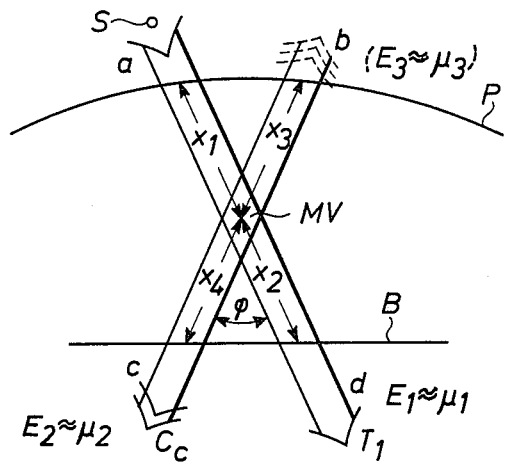
Figure 8:
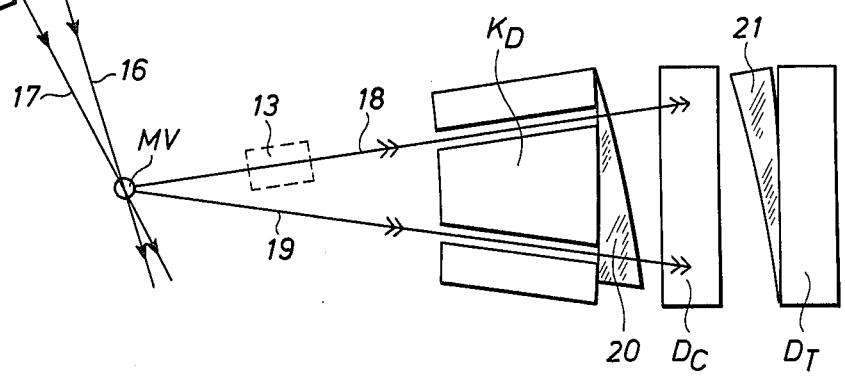

The invention will be described in greater detail below with reference to the accompanying drawings, in which FIG. 1 is a diagrammatic view of a measuring arrangement for the application of the method according to the invention, FIGS. 2, 3, and 4 are partial measuring arrangements as illustrations of a measuring technique with 90° geometry and employment of three different isotopes, FIG. 5 is an arrangement as illustration of a measuring technique with 90° geometry and employment of only one isotope, FIG. 6 is an arrangement as illustration of a measuring technique with arbitrary geometry ($\phi \neq 90°$) and employment of only one isotope, FIG. 7 is an arrangement for the derivation of the wholly generalized formula for the electron density $n$ in a measuring volume MV (equations 1 and 2), and FIG. 8 is a diagrammatic view of collimator comprising more than one radiation source and more than one detector channel.

In FIG. 1, which for the purpose of clarity is very much simplified and without unnecessary details not relevant to the invention, the outer contour of a body, e.g. a patient, is indicated by P, said patient being shown in a horizontal position as for instance placed on a table B.

$E_1$ designates a mono-energetic gamma-quantum emitter (radionucleid) which is so screened by a collimator 1 that a small beam of x-rays 2 is emitted. Said beam of x-rays 2 is directed through the patient P, and the transmitted radiation is measured by a detector in position $d$ (the measure figure for this is $T_1$). Similarly, registering devices are placed in positions $c$ and $b$, which are so screened that only the measuring volume MV is "seen". They register the Compton radiation throughput from the measuring volume MV towards the detectors (the measure figures $C_c$ and $C_b$). With the radiation source $E_1$ placed in position $b$ transmitted radiation 4 can thus be measured in position $c$ (measure figure $T_2$) as also Compton radiation in positions $a$ and $d$ (measure figures $C_a$ and $C_d$). The weight of the collimator, however, makes it inconvenient to move the radiation source back and forth between positions $a$ and $b$. Instead, two radiation sources are used, one in position $a$ and one 5 with a corresponding collimator 6 in position $b$.

The changeover between the radiation sources, then, takes place by means of a rotating sector diaphragm indicated by 7. The angle between the radiation directions 2 and 4 is designated by $\phi$.

For the derivation of equation 1 as stated above the procedure is described below. The description, furthermore, leads to the measuring arrangement according to the invention. In FIG. 2 $S_1$ is a radiation source (e.g. radio-nucleid) which is so screened that it produces a narrow beam of rays of high energy monochromatic radiation through the patient P. The detectors 8 and 9 (e.g. scintillation apparatus) are placed in positions $b$ and $c$ in connection with collimators (not shown) in such a way that they only "see" the measuring volume MV and, moreover, in such a way that their "visual axes" are respectively coincident with and at right angles to the radiation path produced by $S_1$.

The x-ray photons registered by the detectors in positions $b$ and $c$ arise from the Compton scatter of the high energy radiation during its passage through the measuring volume MV. These secondary photons scattering in the direction of the detectors in $b$ and $c$ will have an energy which is well-defined and lower than the primary radiation, and as the scatter angle is 90° for photons both in the radiation path MV – $c$ and in MV – $b$ the intensities of the secondary radiation in both directions ($b$ and $c$) will be equal at the departure from MV (as will the photon energy).

If $E_1$ designates the photon energy in the primary radiation path the quantum in the secondary radiation paths is defined as follows:

$$E_2 = E_1 \frac{1}{1 + \alpha(1 - \cos\phi)},$$

where $$\alpha = \frac{E_1}{mc^2},$$

where $mc^2$ is the stationary energy of the electron, and where, in this case with $\phi = 90°$ is obtained $$E_2 = \frac{E_1}{1 + \alpha}$$

Let the flux of secondary photons (flux is here defined as photons/time unit) emitted from MV in the directions $b$, $c$ be $C^x$. Because of the absorption of radiation in the radiation paths MV – $b$ and MV – $c$, the flux registered by the detectors in positions $b$ and $c$ will be less than $C^x$. For these measure figures termed $C_b$ and $C_c$ the following must be true:

$$C_b = a_1 \cdot C^x$$

$$C_c = a_2 \cdot C^x$$

or $$\frac{C_b}{C_c} = \frac{a_1}{a_2}$$

with $a_1$ and $a_2$ designating so far unknown attenuation factors (less than 1) which are valid for the given quantum energy with respect to the given radiation paths MV – $b$ and MV – $c$. Consequently, if the factor $a_1$ were known it would be possible to calculate the attenuation suffered by a beam of rays of the relevant quantum energy ($E_2$) when passing from MV to the skin surface at $c$ or from $c$ to MV.

In FIG. 3 the arrangement is exactly the same as in FIG. 2 except that the radiation source is placed in position $b$ and now contains a radionucleid with precisely the gamma-quantum energy $E_2$. Moreover, a detector 10 is placed in position $c$ in such a way that it can measure the intensity of the beam of rays produced by $S_2$ after its passage through the skin of the patient.

The detectors 8 and 9, which were before placed in positions $b$ and $c$, are now in FIG. 3 placed in positions $a$ and $d$ in such a way that they now collect secondary quanta leaving MV (arising by the defraction of primary radiation quanta of the energy $E_2$) over the radiation paths MV – $a$ and MV – $d$ (i.e. those which before formed the total primary radiation path in FIG. 2).

The secondary flux ($C^y$) emitted in the directions $a$ and $d$ from MV is defined by $$C^y = K \cdot n \cdot A_o \cdot a_1 \qquad (3)$$

where $K$ is a calibration constant, $n$ is the number of electrons in the measuring volume MV and $A_o$ the primary photon flux which the radiation source $S_2$ directs into the patient, and finally $a_1$ is the attenuation suffered by the primary radiation source quantum before it reaches the measuring volume ($a_1$ in FIG. 1 is the same in FIG. 2).

It must be a precondition for the validity of equation 3 that the only attenuation process within the measuring volume (but NOT outside it) is due to the Compton effect as there would not otherwise be exact proportionality between on the one hand the primary quanta induced into the measuring volume and, on the other, its electron density and the secondary quanta leaving it.

At this stage of the explanation the factor $a_1$ is not yet known.

Let the count figure, which can be measured by means of the detector 10 in position $c$, be $T_1$. It must then be true for $a_3$ since $a_3$ is a factor smaller than 1 to be multiplied by $A_o$ in order to get the exact quantum flux leaving through the skin at $c$ that $$A_o \cdot a_3 = T_1$$

or $$a_3 = \frac{T_1}{A_o}$$

As, however, exactly the same photon energy is employed in the radiation path $b - MV - c$ in FIG. 3 as in FIG. 2 by measuring on scattered radiation originating from MV in the direction $b$ and $c$ the following must be true:

$$a_3 = a_1 \cdot a_2$$

It is therefore now possible to determine $a_1$ and $a_2$ from the following system of equations:

$$\frac{a_1}{a_2} = \frac{C_b}{C_c};$$

$$a_1 \cdot a_2 = \frac{T_1}{A_o}$$

For the count figures $C_a$ and $C_d$ obtained in FIG. 3 the following applies as in FIG. 2:

$$\frac{C_a}{C_d} = \frac{a_4}{a_5}$$

Moreover, the following must be true:

$$C_a = a_4 \cdot C^u$$

The quantum energy ($E_3$) in the radiation path $a - d$ in FIG. 3 must be:

$$E_3 = E_2 \frac{1}{1 + \alpha}$$

as the angle $\phi = 90°$.

In FIG. 4 $S_3$ is a radiation source with gamma-photon energy exactly equal to $E_3$, and the source is of course so screened that the radiation path coincides with the primary radiation path in FIG. 2 (or with the secondary radiation path in FIG. 3).

If the $E_3$-gamma flux in the skin surface at $d$ is termed $A_1$ the following must be true for the quantum flux ($T_2$) measured by a detector 10 placed in position $a$:

$$A_1 \cdot a_6 = T_2$$

or $$a_6 = \frac{T_2}{A_1}$$

By comparing FIG. 3 with FIG. 4 the following equation system can be stated:

$$a_4 \cdot a_5 = \frac{T_2}{A_1}$$

$$\frac{a_4}{a_5} = \frac{C_a}{C_d}$$

From this $a_4$ can be calculated (as can $a_5$), and by inserting this value into the equation $$C_a = a_4 \cdot C^u$$

$C^u$ can be calculated, which will by insertion in equation 3 give a determination of the value of $n$ and so of the electron density of the measuring volume MV.

For the equations so far stated to be valid the only requirement is that the Compton effect in the actual measuring volume is to be the only cause of attenuation of the radiation here. What attenuations take place in the matter surrounding the measuring volume is of no significance whatever for the validity of the equations as stated.

The measuring method described above is thus based on a 90° geometry and employs three different isotopes placed in three different positions and with bilateral measurements in that the scattered radiation is measured on both sides of the patient. This method will hereinafter be designated as method I.

Said method can be changed to another method which is also based on a 90° geometry and bilateral measurements, but where only a single isotope placed in two different positions is used. This method will be designated as method II.

That the equation systems $$a_1 \cdot a_2 = \frac{T_1}{A_o}; \quad \frac{a_1}{a_2} = \frac{C_b}{C_c}$$

and $$a_4 \cdot a_5 = \frac{T_2}{A_1}; \quad \frac{a_4}{a_5} = \frac{C_a}{C_d}$$

are valid is evident from the fact that the energy level for the primary radiation sources used is the same as the energy level for the scattered radiation along the same paths.

In FIG. 5 S stands for the usual radiation source although not, as in FIG. 2 with the quantum energy $E_1$, but with the quantum energy $E_2$. As a consequence, the secondary photon energy in the radiation paths $MV - b$ and $MV - c$ is lower, namely $E_3$ instead of $E_2$.

Let $x_1$ and $x_2$ be the number of electrons/cm$^2$ on the radiation paths $MV - b$ and $MV - c$. For clarity of exposition the radiation paths will be assumed to have a cross section of 1 cm$^2$.

From FIG. 5 the following system of equations can be directly established:

$$a_1^* \cdot a_2^* = a_3^*$$

$$\frac{A_1^*}{A_2^*} = \frac{C_b^*}{C_c^*}$$

where the asterisk indices indicate that the topmost equation should be compared with the corresponding equation from FIG. 3, keeping in mind, though, that $a_3^*$ ($a_1^*$ and $a_2^*$) is NOT the attenuation factor which was measured in FIG. 3, but the attenuation factor which would have been found if in FIG. 3 not the energy $E_2$ had been used, but instead the energy $E_3$.

In the second of these equations the asterisk indices on $C_b^*$ and $C_c^*$ indicate that it is the values actually measured in FIG. 5 which are being employed, i.e. they are not the same figures as measured in FIG. 2.

In order to solve this system of equation it is therefore necessary to find the value of $a_3^*$. The following must be true:

$$A_0 \cdot e^{-(\sigma_1^{E_2})(X_1 + X_2)} = T_1, \text{where}$$

where $\sigma_1^{E_2}$ designates the effective cross section and thereby also the probability that a photon with the energy $E_2$ is removed from a radiation path containing one electron/cm². $\sigma_1^{E_2}$ can then be understood as the expression for "the total linear absorption coefficient" measured in arbitrary unit.

Taking the natural logarithm on both sides we get:

$$-\sigma_1^{E_2}(X_1 + X_2) = \ln T_1 - \ln A_0$$

$$X_1 + X_2 = \frac{\ln A_0 - \ln T_1}{\sigma_1^{E_2}}$$

This means that it is possible in FIG. 3 to determine the electron quantity in the radiation path $b - MV - c$ if $\sigma_1^{E_2}$ is previously known (table). This latter calculation presupposes for its validity that "the photons cannot see to which type of atom (atom number) the electrons belong". That is to say that the probability per electron of the photon being removed from its radiation path is exactly the same, irrespective of the electron system type with which it interacts.

Practically, this implies that $E_2$ must be sufficiently high so that no photoelectric processes will arise in the matter (tissue) surrounding the measuring volume, but at the same time not so high that the pairproduction effect comes into action. (In the case of human tissue the atom number of which is generally below 7 (N), $E_2$ should then be between about 100 KeV and 1.02 Mev).

Precisely here the total linear absorption coefficient will be independent of the atom number of the matter (within the stated limits) and will thus depend only on the number of electrons and on the quantum energy.

Given this condition it is then possible to calculate the $a_3^*$ to be employed in FIG. 5 since a table can supply the value which applies for $\sigma_1^{E_3}$ when $E = E_3$ and not, as in FIG. 3, $E = E_2$:

$$a_3^* = e^{-(x_1 + x_2) \cdot (\sigma_1^{E_3})}$$

Accordingly, $a_1^*$ and $a_2^*$ in FIG. 5 can be determined, but for these attenuation factors it is known that:

$$a_1^* = e^{-(x_1)(\sigma_1^{E_3})}$$

$$a_2^* = e^{-(x_2)(\sigma_1^{E_3})}$$

and $a_1^*$ can now be transformed to e.g. $a_1$:

$$\ln a_1 = -x_1 \cdot \sigma_1^{E_3} =$$

$$x_1 = \frac{-\ln a_1^*}{\sigma_1^{E_3}}$$

$$a_1 = e^{-x_1(\sigma_1^{E_2})}$$

$a_1$ is therefore determined through employment of the arrangement shown in FIGS. 5 and 3.

In a completely analogous manner, $a_4$ can be determined by repetition of the arrangement in FIG. 4 though not with the radiation source $S_3$ with energy $E_3$, but with $E_2$.

A method has thus been established for measuring the electron density of a part volume by placing one isotope (with the quantum energy $E_2$) in position $a$ and subsequently $b$ and by successively measuring the scattered radiation in the positions $b - c/a - d$. This is method II.

Now the reflection angle $\phi$ is changed from 90° to an arbitrary angle as shown in FIG. 6.

The radiation source S in position $a$ via its passage through MV produces secondary radiation along the paths $MV - b$ and $MV - c$, and the transmitted primary radiation can be measured in position $d$ ($T_1$).

The quantum energies in the secondary radiation paths can be calculated in the usual way. The relevant total linear absorption coefficients (or $\sigma_1^E$) can then be determined (table). For the count figures in the detectors placed in positions $b$ and $c$ the following must be true:

$$C_b = C^z \cdot e^{-\mu_3 X_1}$$

$$C_c = C^q \cdot e^{-\mu_4 X_2}$$

where $C^z$ and $C^q$ designate the count figures that would have been obtained in the detectors $b, c$, if no attenuation of the secondary quanta had taken place during their passage from MV to the detector in position $b$ and position $c$ respectively. With 90° geometry $C^q = C^z$ because of the symmetrical spatial distribution of the secondary quanta around the travelling direction of the primary quanta. As this spatial distribution is not, however, symmetrical with respect to a plane at right angels to the travelling direction $C^q \neq C^z$ is implied when $\phi \neq 90°$.

The relation $C^z/C^q$ can also be obtained from tables (or can be assessed in the calibration constant) so that the above equations can be restated as follows:

$$\frac{C_b}{C_c} = K_1 \cdot e^{-(\mu_3 X_1 - \mu_4 X_2)}$$

If the radiation source S ($E_1$) is now removed to position $b$ in FIG. 6 the correctness is obvious of the equation:

$$A_0 \cdot e^{-\mu_1 (X_1 + X_2)} = T_2$$

$$e^{-\mu_1(X_1 + X_2)} = \frac{T_2}{A_0} \qquad (3)$$

The following system of equations can therefore be stated:

$$\frac{C_b}{C_c} = K_1 \cdot e^{-\mu_3 X_1 + \mu_4 X_2}$$

$$\frac{T_2}{A_0} = e^{-\mu_1(X_1 + X_2)}$$

Since $K_1$, $\mu_1$, $\mu_2$, and $\mu_3$ are known from tables, and as $A_o$, $C_b$, $C_c$, and $T_2$ are measured quantities this system of equations permits a determination of $x_1$ and $x_2$.

If the procedure is repeated from the beginning with the radiation source in position b and transmissions $T_1$, $C_a$, and $C_d$ are measured it is clearly possible to determine the electron density of the measuring volume in a manner corresponding to method II but now with arbitrary geometry. This is method III.

From FIG. 7 it is apparent that the following system of equations can be stated for this latter method whereby a formula is obtained for the determination of $n$, in that $K$ (with varying indices) designates constants and all other symbols are employed as before:

$$n \cdot K_1 \cdot K_0 \cdot e^{-\mu_1 \cdot x_1} = C_a$$
$$n \cdot K_2 \cdot K_0 \cdot e^{-\mu_2 \cdot x_2} = C_d$$
$$A_0 \cdot e^{-\mu_1(x_1 + x_2)} = T_1$$
$$n \cdot K_1 \cdot K_3 \cdot e^{-\mu_3 \cdot x_3} = C_b$$
$$n \cdot K_2 \cdot K_3 \cdot e^{-\mu_2 \cdot x_4} = C_c$$
$$A_0 \cdot e^{-\mu_1(x_3 + x_4)} = T_2$$

This entire system of equations can be solved.

The solution of the system of equations with regard to n is as follows:

$$n = K[C_a \cdot C_b \cdot C_c \cdot C_d]^{1/4} \left[ \frac{C_c \cdot C_d}{C_a \cdot C_b} \right]^{\frac{2\mu_1 + \mu_3 - \mu_2}{4(\mu_2 + \mu_3)}} \left[ \frac{A_0^2}{T_1 \cdot T_2} \right]^{\frac{\mu_2(\mu_1 + \mu_3)}{2\mu_1(\mu_2 + \mu_3)}} [A_0]^{-1}$$

In this equation all exponents are positive (not proved here). It follows that the measure figures $C_a$ and $C_b$ will occur with a smaller exponent than the measure values $C_d$ and $C_c$, namely:

$$\underbrace{\phantom{xxxx}}_{C_a, C_b} \quad \frac{1}{4} - \beta$$

and $$\underbrace{\phantom{xxxx}}_{C_c, C_d} \quad \frac{1}{4} + \beta$$

where $$\beta = \frac{2\mu_1 + \mu_3 - \mu_2}{4(\mu_2 + \mu_3)}$$

If, by a suitable selection of gamma quantum energy of the radiation source and of refraction angle $\phi$ it were possible to obtain a value for $\beta$ very close to (but in fact a little below) ¼ then this would mean that the product $C_a \cdot C_b$ in the equation would have an exponent very nearly equal to 0 and would thus always assume the value 1 regardless of the measured values for $C_a$ and $C_b$.

In this case the equation would be reduced as follows:

$$n = k \cdot [C_c \cdot C_d]^{\frac{\mu_1 + \mu_3}{2(\mu_2 + \mu_3)}} \left[ \frac{A_0^2}{T_1 \cdot T_2} \right]^{\frac{\mu_2(\mu_1 + \mu_3)}{2\mu_1(\mu_2 + \mu_3)}} [A_0]^{-1}$$

an equation which would closely approach the simple formula (limit value):

$$n = \left[ \frac{C_c \cdot C_d}{(T_1 \cdot T_2)^{\mu_2/\mu_1}} \right]^{1/2} \cdot K$$

This is not wishful thinking, but fact.

If $C_s^{137}$ ($E_1 = 0.662$ Mev.) is chosen as the radionucleid we obtain the value of ¼ $- \beta = 0.02728$ in the case of $\phi = 45°$. For $\phi = 30°$ we get: ¼ $- \beta = 0.01357$.

This value is sufficiently close to 0 for the product $(C_a \cdot C_b)^{1/4 - \beta}$ to be practically constant ($\approx 1$) in measurements on human bodies.

The last method described is thus based on arbitrary geometry with employment of a single isotope placed in two different positions, and where measurements are made on only one side of the patient.

The theoretical basis of the method may be seen as rather complicated, but the measuring technique itself is simple.

Thus a radiological method for the measurement of the electron density of a part volume has been described. Basically, its idea is in the employment of three different isotopes, each with its own well-defined gamma energy. These isotopes are extra-corporally so placed that primary as well as secondary beams of x-rays will arise in the organism. Moreover, the radiation sources and the measuring apparatus are so arranged that at completion of measurement the primary and secondary radiaton paths coincide and that each of them for single measurements is at right angles to the other. This method permits a determination of the electron density of the part volume provided that only Compton processes take place inside the volume itself and quite independently of the matter surrounding the volume.

This rather clumsy measuring arrangement can by mathematical means be reduced to a much more elegant method employing only a single radio isotope of suitable characteristics, said isotope being placed in only two different positions and permitting measurement of the electron density in the part volume by extra-corporal measurements on only one side (opposite side) of the patient if and when the patient is assumed not to contain a substantial amount of matter with an atomic number so high that photo-electric effects will occur.

The radiological measuring methods first described permit a determination of the attenuation suffered by an ionizing beam of x-rays during passage from one arbitrary point in a body to another, and also, of course, a measurement of the electron density of the part volume.

The last measuring arrangement described permits an indication of only the electron density of the part volume.

Conclusive to this discussion it will be understood that the several measuring principles outlined here are in fact so closely related that it is in principle a case of only one radiological measuring method with several variants.

Finally, a specific problem will be briefly discussed concerning the design of the collimators for the obviously practical employment of more than one radiation source affording a greater radiation power as well as a reduced exposure time so that the scanning procedure can be made reasonably quick.

FIG. 8 shows a pair of collimators, i.e. a radiation source collimator $K_S$ and a detector collimator $K_D$ having slits which are so arranged as to focus these collimators on the measuring volume MV. For simplicity, the radiation source collimator is shown with only two channels 14 and 15 respectively, each with its own radiation source, while a greater number of radiation sources is of course possible. The radiation sources produce the primary radiation paths 16 and 17 while the secondary radiation paths are numbered 18 and 19 respectively. Said secondary radiations paths pass through corresponding slits in the detector collimator $K_D$ and hit the corresponding detector crystal for the count figures $C_i$, said crystal being designated as $D_C$. As channel 19 forms a smaller angle to the radiation source channels 14 and 15 respectively than does the uppermost channel 18 the flux through the detector channel 19 will be greater than in the upper channel 18, cf. the fact that the probability of a quantum scattering in the forward direction is greater than in the backward direction. The secondary radiation is thus no longer a mono-energetic radiation, but even in the case of considerable fan-shape of the collimators the spectral width measured as the change in $\mu_2$ over the spectrum will be small.

If the flux in channel 18 is supposed to correspond to the figure 80 and that in channel 19 to 100 the count figure in the detector $D_C$ will be 180.

An inhomogeneity 13 is now introduced in the secondary radiation path 18 increasing the absorption in this radiation path by e.g. 10%.

The flux into the detector $D_C$ is now:

$$180 - \frac{10 \cdot 80}{100} = 172$$

If the inhomogeneity 13 is now transferred to the other secondary radiation path 19 the count figure is still to be 172 according to the mathematical basis of the method.

As the change in $\mu_2$ over the spectrum is again regarded as nigligible the count figure in the detector $D_C$ will be:

$$180 - \frac{10 \cdot 100}{100} = 170$$

which is different from the figure given below.

This problem is solved by inserting a wedge-shaped absorption body 20 in front of the detector $D_C$. The thickness of this wedge is to be 0 for the uppermost secondary radiation path 18. The flux here therefore remains 80 into the detector.

For the other secondary radiation path 19 the thickness should be such that the flux into the detector $D_C$ at this point is reduced from 100 to 80. The count figures in the detector $D_C$ is then without inhomogeneity $80 + 80 = 160$.

With the inhomogeneity 13 placed in the uppermost secondary radiation path 18 the count figure now becomes:

$$80 - \frac{10 \cdot 80}{100} + 80 = 152.$$

With the inhomogeneity 13 placed in the other secondary radiation path 19 the count figure becomes:

$$80 + 80 - \frac{10 \cdot 80}{100} = 152$$

which is in accordance with the theoretical value. By introducing this detector-wedge system an error is now introduced into the count figure for the transmitted primary radiation, a problem which is solved by placing yet another wedge 21 behind the detector $D_C$, as shown in the figure.

This hindmost wedge must be so shaped that the entire system consisting of the front wedge 20, the detector $D_C$, and the hindmost wedge 21 functions with regard to the primary radiation as a plane-parallel filter with respect to the collection of beams. The correct count figure for transmitted radiation can now be produced by yet another detector $D_T$ placed behind the wedge 21. The exact dimensions of the wedge can be calculated in a computer.

Concerning the individual elements of the apparatus it can be mentioned for instance that the detector collimators are designed as 40 cm long fan-shaped leaden blocks with a base of 10 cm × 30 cm. The radiation sources consist of two sets of needle-shaped $Cs^{137}$ pins (0.662 MeV, 2 × 50 Ci).

The detectors for the measurement of $C_c$, $C_d$ consist of 2 × 3 NaI (6 inches) crystals with associated electronics with impluse amplitude analyzer as well as two liquid scintillation detectors for the measurement of $T_1$ and $T_2$. A main defraction angle $\phi = 38°$ and for MV a diameter of 7.2 mm and a length of 15 mm is chosen.

The screening system built into the collimators should be 2 × 3 rotating sector diaphragms made of lead.

The exposure time would then be about 50 sec. for the count figure $C_c$ $(C_d) = 2 \times 10^5$ and should be followed by a calibration time of 2 minutes. The patient dosage can thus be estimated at 0.1 Rad in the measuring volume and considerable less in the skin surface.

With the here described measuring arrangement, and even in the presence of considerable inhomogeneities round the measuring volume MV it should be possible — taking into account the biological variance on the electron density (2 o/oo) of pathological processes — to differentiate between these provided that their electron densities differ by 6 – 10 o/oo.

In the following a tentative list will be given of the diffential diagnosis which should hereby be made possible although admittedly present knowledge of the electron density of the tissues in question is incomplete. Where the contrast can be assessed with a high probability or has been actually measured it is within the brackets followed by —, and in the remaining cases the estimate is based upon the pathological-anatomic picture of the structures concerned and should thus be taken as tentative.

Head (Central Nervous System)

1. Ventricle delatation (26 o/oo — )
2. Epidural hematomas (27 o/oo — ) Normal cortex
3. Subdural hematomas (20 o/oo — ) Normal Cortex
4. Cystic cerebellar astrocytoma (12 o/oo — ) Normal cerebellar tissue
5. Metastases (10 o/oo — ) Normal tissue
6. Gliobastoma (10 o/oo) Metastasis
7. Meningioma (25 o/oo) Metastasis
8. Meningioma (35 o/oo) Glioblastoma
9. Vascular malformation (14 o/oo) Metastasis
10. Meningioma (12 o/oo) Vascular malformation
11. Neurinoma (35 o/oo) Meningioma
12. CNS-sarcoma (15 o/oo) Normal CNS tissue
13. Glioblastoma (20 o/oo) Hematoma
14. Cystic astrocytoma (10 o/oo — ) Medulloblastoma
15. Comophobic pituitary adenoma (10–20 o/oo) Eosinophilic (basophilic) adenoma
16. Cranial pharyngeoma (40 o/oo) Cromophobic adenoma
17. Epidermoid (25 o/oo) Meningioma
18. Epidermoid (10 o/oo) Neurinoma
19. Brainstem glioma (15 o/oo) Angioreticuloma
20. Acute hematomas (25 o/oo — ) Normal white substance
21. Porencephaly (10 o/oo) Normal spinal fluid
22. Sheenan's syndrome (10 o/oo) Normal adenopituitary

Neck

1. Thyroid cyst (15 o/oo — ) Cold modules
2. Thyroid cancer (20 o/oo) Riedel struma

Thorax

Oesophagus

1. Cardiospasm (14 o/oo — ) Cancer oesophagi

Mediastinum

1. Metastase in gldd. around carina (30 o/oo — ) Normal gldd.
2. Cyst (30 o/oo) Aorta aneurism
3. Lymfosarcoma (15 o/oo) Glld metastasis
4. Lipoma (70 o/oo — ) specific diagnosis
5. Thymoma (15 o/oo) Rectro-sternal struma
6. Thymoma (10 o/oo) Invasive metastasing from bronch. ca.
7. Fibroma (5 o/oo — ) specific diagnosis
8. Teratoma (10 o/oo) Cyst
9. Teratoma (50 o/oo) Aorta aneurism

Cor

1. Pericardial lipoma (110 o/oo — ) Mesothelioma
2. Pericardial cyst (100 o/oo — ) Lipoma
3. Ectasia cordis (20 o/oo — ) Hydropericardium
4. Myocardial fatty degen. (10 o/oo) Normal myocardium
5. Myocardial fibrosis (10 o/oo) Normal myocardium
6. Pericardial fibroma (50 o/oo) Mesothelioma
7. Pericardial cyst (70 o/oo — ) Pericardial fibroma
8. Pericardial lipoma (150 o/oo — ) Pericardial fibroma

Pulmonary parenchyma

1. Varied picture of the spread and development of Emphysema (—)
2. Hamartoma (50 o/oo — ) Metastasis
3. Hamartoma (50 o/oo — ) Cancer pulm.

Pleura

1. Pleural mesothelioma (50 o/oo) Fibroma
2. Neurinoma (10 o/oo) Metastasis

Abdomen

Liver

1. Steatosis Hepatis (0–50 o/oo — ) Normal liver tissue
2. Cirrhosis hepatis (0–20 o/oo — ) Normal liver tissue
3. Metastasis (10 o/oo — ) Normal liver tissue
4. Liver abscess (10 o/oo) Liver cyst
5. Liver abscess (25 o/oo — ) Normal liver tissue
6. Amyloidosis hepatis (7 o/oo) Normal liver tissue
7. Cirrhosis hepasis (10 o/oo — ) Steatosis hepatis

Stomach

1. Fundus cancer (14 o/oo — ) Normal surrounding liver tissue
2. Vent. reticulosarcoma (20 o/oo) Linitis plastica
3. Vent. fibroma (20 o/oo — ) Lymphoglandular metastasis
4. Vent. neurinoma (10 o/oo) Vent. fibroma
5. Leiomyoma (10 o/oo) Neurinoma
6. Leiomyoma (20 o/oo) Fibroma
7. Adenocarcinoma (20 o/oo — ) Fibroma
8. Adenocarcinoma (15 o/oo) Neurinoma
9. Adenocarcinoma (10 o/oo) Leiomyoma

Pancreas

1. Acute pancreatitis (10 o/oo) Normal pancreas
2. Chr. pancreatitis (25 o/oo — ) Normal pancreas
3. Ca. pancreatis (15 o/oo) Chr. pancreatitis
4. Acute pancreatitis (10 o/oo) Ca. pancreatis
5. Ca. pancreatis (10 o/oo) Normal pancreas
6. Pseudo-cyst (20 o/oo — ) Ca. Pancreatis

Kidneys

1. Hypernephroma (20 o/oo — ) Solitary renal cyst
2. Ellis Type I, stage II (7 o/oo) Ellis type I, stage III
3. Amyloidosis renis (7 o/oo) Normal renal tissue

Suprarenal glands

1. Neuroblastoma (10 o/oo) Solitary renal cyst
2. Phaechromocytoma (20 o/oo) Solitary renal cyst
3. Amyloidosis (7 o/oo) Normal cortex
4. Phechromocytoma (15 o/oo) Neuroblastoma
5. Suprarenal haemorrhage (10 o/oo) Normal tissue
6. Suprarenal metastasis (10 o/oo — ) Normal tissue
7. Suprarenal haemorrhage (15 o/oo — ) Metastasis

Small Intestine

1. Lymphosarcoma (10 o/oo) Adenocarcinoma
2. Mucocele appendix (15 o/oo) Cancer coeci
3. Mucocele appendix (15 o/oo) Argentafinoma appendix
4. Cancer coeci (20 o/oo — ) Faecalia

Gross Intestine

1. Periappendicular abscess (20 o/oo — ) Oment

2. Diverticulitis (15 o/oo) Adenocarcinoma
3. Benign stricture (20 o/oo) Malign stricture Genitals 1. Brenner tumor (> 15 o/oo — ) Specific diagnosis
2. Teratoma ovarii (< 10 o/oo) Specific diagnosis
3. Granulosa-thecacelle tumor (10 o/oo) Cystic ovarial tumors Other diagnoses 1. Osteodensitometry
2. Pelvic enchondroma (70 o/oo — ) Bone cyst
3. Crural hernia (20 o/oo) Adenitis gldd. inguinales.

To this list of diagnoses the following conclusions can be added:

If the here described method is used with a patient whose clinical condition does not otherwise on the whole indicate any particular diagnosis the result will be, "such and such pathological conditions are possible whereas there is little probability of the following diseases and the following others can be entirely excluded".

In some cases, however, it will even in this situation be possible to state a quite specific diagnosis.

If, on the other hand, the method is applied with a patient for whom a diagnosis is considered on the whole probable the result of the examination could be, "the proposed diagnosis is radiobiopmetrically probable", but in some cases we shall find (and these are the ones that justify the examination) that the diagnosis made is not probable whereas the following conditions should reasonably be taken into consideration.

The most fortunate situations, of course, are those in which the clinical problem coincides with one of the "pairs" in the list of differential diagnoses.

It seems probable that the method could yield particularly promising results from scanning or taking radiobiopsies on the liver, the pancreas, the kidneys, or intercranially.

SUMMARY

A complex radiological measuring method has been described according to which the electron density of an anatomic structure the size of a pea can be assessed by means of extra-corporally positioned and screened radionucleids ($Cs^{137}$, 2 × 50 Ci) and detectors.

On the basis of a contrast of at least 6 – 10 o/oo a list of nearly one hundred "pairs" has been drawn up, of which the differential diagnosis must now be considered feasible from the contents of the measuring volume. Thus the method should make possible a differentiation between several benign pathological conditions and between malign diseases and benign ones. A particularly optimistic view is taken with regard to the examination results for the pancreas, liver, kidney, and the central nervous system.

I claim:

1. A method for the determination of the electron density of desired small volumes, called the measuring volume, of a body comprising the steps of directing a first beam of ionizing radiation through said measuring volume to penetrate said volume in a first direction, said first beam having an intensity $I_0$; measuring extra-corporally the intensity of the primary radiation and the intensity of scattered radiation in a second direction of the radiation of said first beam transmitted through said volume, said second direction forming an angle $\phi$ to said first direction; directing a second beam of ionizing radiation substantially of said intensity $I_0$ through said volume in said second direction; measuring extra-corporally the intensity of the primary radiation and the scattered radiation in said first direction of the radiation of said second beam transmitted through said volume in said second direction, employing such high energy radiation that the Compton effect will be the wholly dominant absorption phenomenon in said volume and in the radiation paths in said first and second direction, and that the change in the absorption cross-section from primary to secondary radiation caused by the Compton shift will be substantial; and employing the values of said measured intensities to calculate the electron density of said measuring volume in accordance with the formula:

$$n = K[C_c \cdot C_d]^{\frac{\mu_1 + \mu_3}{2(\mu_2 + \mu_3)}} \cdot \left[\frac{A_0^2}{T_1 \cdot T_2}\right]^{\frac{\mu_2(\mu_1+\mu_3)}{2\mu_1(\mu_2+\mu_3)}} \cdot [A_0]^{-1}$$

where
$n$ = electron density
$K$ = a calibration constant
$\mu_1$ = the total linear attenuation coefficient for primary radiation
$\mu_2$ = the total linear attenuation coefficient for Compton radiation "forwards"
$\mu_3$ = the total linear attenuation coefficient for compton radiation "backwards"
$A_0$ = arbitrary expression for the power of the radiation source
$C_c$ = measure of Compton radiation
$C_d$ = measure of Compton radiation
$T_1$ = measure of Transmitted Radiation
$T_2$ = measure of Transmitted Radiation.

2. A method as claimed in claim 1, in which said angle preferably lies within the interval of 30°– 60° and in which the radiation source is chosen to be $Cs^{137}$.

3. A method as claimed in claim 1, in which the secondary radiation is measured in another direction than in the direction of the primary radiation and is measured on diametrically opposed sides of said measuring volume.

4. A method as claimed in claim 1, in which a number of measure volumes is successively penetrated by a series of radiation beams, whereby corresponding intensities are measured in such a way that paired measure values are obtained, on the basis of which the electron densities of the measuring volumes within a certain desired area can be determined.

5. A method as claimed in claim 1, in which said angle preferably lies within the interval of 30°– 60°, and in which the radiation source is chosen to be $Co^{60}$.

6. An apparatus for the determination of the electron density of desired small volumes, called the measuring volume, of a body, the apparatus comprising a first and second radiation source for the successive emission of a first and a second beam of ionizing radiation directed towards a partial volume to be examined, the measuring volume, which first and second beams together form a certain angle $\phi$, means for alternately screening said first and second radiation source, a first detector placed diametrically opposite the first radiation source with respect to the measuring volume for measuring the intensity of the transmitted primary radiation from said first radiation source, a second detector placed in the radiation path of said second radiation source for measuring the intensity of said secondary radiation originating from said first primary radiation transmission through said measuring volume, as well as a third detector placed in the radiation path of said first radiation beam for measuring the intensity of said secondary radiation originating from said second primary radiation transmission through the measuring volume, and a fourth detector for measuring the intensity of the transmitted primary radiation from the second radiation source; means for registering the measured values, said apparatus further comprising means for producing a radiation of such high energy that the Compton effect will be the wholly dominant absorption phenomenon in the measuring volume and in the primary and secondary radiation paths, and that the change in the absorption cross-section from primary to secondary radiation caused by the Compton shift will be substantial.

7. An apparatus as claimed in claim 6, the apparatus further comprising two detectors being positioned in the rear extensions of the radiation paths for measuring backward scattered radiation.

8. An apparatus as claimed in claims 6, the apparatus further comprising means for processing the values measured for the calculation of the electron density in said volume as well as means for displaying the result.

9. An apparatus as claimed in claim 8, the apparatus further comprising means for successively scanning a number of measuring volumes such that paired measure values are obtained; on the basis of which the electron densities of the measuring volumes within a certain desired area can be determined.

* * * * *